US010918589B2

(12) United States Patent
Goepfert

(10) Patent No.: US 10,918,589 B2
(45) Date of Patent: Feb. 16, 2021

(54) PERSONAL-LUBRICATING MATERIAL AND METHOD FOR LUBRICANT MANUFACTURE

(71) Applicant: John Robert Goepfert, Janesville, WI (US)

(72) Inventor: John Robert Goepfert, Janesville, WI (US)

(*) Notice: Subject to any disclaimer, the term of this patent is extended or adjusted under 35 U.S.C. 154(b) by 0 days.

(21) Appl. No.: 14/214,768

(22) Filed: Mar. 15, 2014

(65) Prior Publication Data

US 2015/0258009 A1 Sep. 17, 2015
US 2019/0151226 A9 May 23, 2019

Related U.S. Application Data

(60) Provisional application No. 61/793,322, filed on Mar. 15, 2013.

(51) Int. Cl.
A61K 8/92 (2006.01)
A61K 8/73 (2006.01)
A61K 8/34 (2006.01)
A61Q 19/00 (2006.01)
A61Q 17/00 (2006.01)

(52) U.S. Cl.
CPC .............. A61K 8/922 (2013.01); A61K 8/345 (2013.01); A61K 8/73 (2013.01); A61Q 17/005 (2013.01); A61Q 19/00 (2013.01); A61K 2800/48 (2013.01); A61K 2800/548 (2013.01)

(58) Field of Classification Search
CPC .......... A61K 8/922; A61K 8/345; A61K 8/73; A61Q 19/00
USPC .......................................................... 514/54
See application file for complete search history.

(56) References Cited

U.S. PATENT DOCUMENTS

| 4,357,258 | A | * | 11/1982 | Haag ...................... A01N 25/04 516/58 |
| 5,190,915 | A | * | 3/1993 | Behan .................. A61K 8/0295 424/49 |
| 5,512,289 | A | | 4/1996 | Tseng et al. |
| 5,986,119 | A | * | 11/1999 | O'Lenick, Jr. .......... C07C 67/02 426/417 |
| 6,162,447 | A | * | 12/2000 | Fankhauser ............ A61K 8/068 424/401 |
| 6,531,125 | B1 | | 3/2003 | Borgford |
| 6,635,702 | B1 | * | 10/2003 | Schmucker-Castner ..................... A61K 8/365 524/291 |
| 7,285,517 | B2 | | 10/2007 | Ahmad et al. |
| 7,378,479 | B2 | | 5/2008 | Tamareselvy et al. |
| 7,423,082 | B2 | | 9/2008 | Lai et al. |
| 8,021,650 | B2 | | 9/2011 | Tamareselvy et al. |
| 8,029,812 | B2 | | 10/2011 | Sunkara |
| 8,044,156 | B2 | | 10/2011 | Tamareselvy et al. |
| 8,343,945 | B2 | | 1/2013 | Tamarkin et al. |
| 8,486,374 | B2 | | 7/2013 | Tamarkin et al. |
| 8,518,376 | B2 | | 8/2013 | Tamarkin et al. |
| 8,540,970 | B2 | | 9/2013 | Rodriguez-Vilaboa |
| 8,636,982 | B2 | | 1/2014 | Tamarkin et al. |
| 8,668,913 | B2 | | 3/2014 | Ahmad et al. |
| 2007/0241306 | A1 | * | 10/2007 | Wehner ................... A61Q 5/02 252/67 |
| 2009/0304787 | A1 | * | 12/2009 | Odidi ................... A61K 9/1611 424/452 |
| 2010/0021409 | A1 | * | 1/2010 | Alwattari ............... A61K 8/416 424/70.13 |
| 2012/0021111 | A1 | * | 1/2012 | Pfister ....................... A23L 2/60 426/548 |
| 2013/0171078 | A1 | * | 7/2013 | Lawson ................... A61Q 1/06 424/59 |

OTHER PUBLICATIONS

Knoepfler et al, Agri. Food Chem., 1958, 6(2), 118-121.*
Momoh et al, Bull. Environ. Pharmacol. Life Sci., 2012, 1(10), 21-27.*
Abdel-Wahhab, Mosaad A., et al. "Dietary incorporation of jojoba extract eliminates oxidative damage in livers of rats fed fumonisin-contaminated diet." *Hepatoma Research* 2 (2016): 78-86.
Al-Mamun, M. Abdulla et al. "Characterization and Evaluation of Antibacterial and Antiproliferative Activities of Crude Protein Extracts Isolated from the Seed of *Ricinus Communis* in Bangladesh." *BMC Complementary and Alternative Medicine* 16 (2016): 211. PMC. Web. Jan. 4, 2018.
Ayuba, L., et al. "Efficacy of Castor Oil in the Control of Throat; Skin and Enteric Bacteria." (2017).
Brennan, Patrick J., et al. "Metabolism of galactose in herpes simplex virus-infected cells." *Virology* 69.1 (1976): 216-228. http://www.sciencedirect.com/science/article/pii/0042682276902087.
Chaddock, John A., et al. "Major Structural Differences between Pokeweed Antiviral Protein and Ricin A-Chain do not Account for their Differing Ribosome Specificity." *The FEBS Journal* 235.1-2 (1996): 159-166.
Chen, Yan, et al. "Acute inhibition of Ca2+/calmodulin-dependent protein kinase II reverses experimental neuropathic pain in mice." *Journal of Pharmacology and Experimental Therapeutics* 330.2 (2009): 650-659.
Goodsell, David. "Ricin | Molecule of the Month." *PDB-101: Ricin*, The Scripps Research Institute and the RCSB PDB, May 2013, pdb101.rcsb.org/motm/161.
Habashy, Ramy R., et al. "Anti-inflammatory effects of jojoba liquid wax in experimental models." *Pharmacological research* 51.2 (2005): 95-105 http://www.sciencedirect.com/science/article/pii/S1043661804001148?via%3Dihub.
Hawley, Simon A., et al. "The ancient drug salicylate directly activates AMP-activated protein kinase." *Science* 336.6083 (2012): 918-922.

(Continued)

*Primary Examiner* — Ganapathy Krishnan
(74) *Attorney, Agent, or Firm* — Daniel A. Blasiole; Craig A. Fieschko, Esq.; DeWitt LLP

(57) ABSTRACT

The invention relates to a novel composition and method of manufacturing personal lubricant, commonly known as lube, to combine the most desirable features of disparate existing lube compositions to create a long lasting, oil-based, water soluble, non-toxic, anti-microbial, anti-yeast, non-staining, personal lubricant that can be organically sourced and will not damage commonly used prophylactics.

15 Claims, No Drawings

(56) References Cited

OTHER PUBLICATIONS

Jackson, Kia J., and M. Imad Damaj. "Calcium/calmodulin-dependent protein kinase IV mediates acute nicotine-induced antinociception in acute thermal pain tests." *Behavioural pharmacology* 24.8 (2013).

Kumarasamy, Ramasamy, and Herbert A. Blough. "Galactose-rich glycoproteins are on the cell surface of herpes virus-infected cells: 1. Surface labeling and serial lectin binding studies of Asn-linked oligosaccharides of glycoprotein gC." *Archives of biochemistry and biophysics* 236.2 (1985): 593-602. http://www.sciencedirect.com/science/article/pii/0003986185906630.

Laderoute, Keith R., et al. "5'-AMP-activated protein kinase (AMPK) is induced by low-oxygen and glucose deprivation conditions found in solid-tumor microenvironments." *Molecular and cellular biology* 26.14 (2006): 5336-5347.

Ligament World Co. ,Ltd. "1-3-2. Sebum membrane." *LIGAMENT WORLD Co.,Ltd.*, www.ligament.co.jp/trouble/skin9e.htm.

Maroon, Joseph C., Jeffrey W. Bost, and Adara Maroon. "Natural anti-inflammatory agents for pain relief" *Surgical neurology international* 1 (2010).

McKeon, Thomas A., Stephanie A. Patfield, and Xiaohua He. "Evaluation of castor oil samples for potential toxin contamination." *Journal of the American Oil Chemists' Society*93.2 (2016): 299-301. https://link.springer.com/article/10.1007/s11746-015-2766-5.

Nakashima, K., Takeuchi, K., Chihara, K., Hotta, H. and Sada, K. "Inhibition of hepatitis C virus replication through adenosine monophosphate-activated protein kinase-dependent and -independent pathways." *Microbiology and Immunology* (2011), 55: 774-782. doi:10.1111/j.1348-0421.2011.00382.x.

Natural Standard. "Jojoba (Simmondsia chinensis) | Plant Profiler." *Sigma-Aldrich*, www.sigmaaldrich.com/life-science/nutrition-research/learning-center/plant-profiler/simmondsia-chinensis.html.

Orgel, O., & Joseph, P. R. (2006). Surface-active helices in transmembrane proteins. *Current Protein and Peptide Science*, 7(6), 553-560.

Prajapati, Hetal N., Damon M. Dalrymple, and Abu TM Serajuddin. "A comparative evaluation of mono-, di-and triglyceride of medium chain fatty acids by lipid/surfactant/water phase diagram, solubility determination and dispersion testing for application in pharmaceutical dosage form development." *Pharmaceutical research* 29.1 (2012): 285-305.

Prantner, Daniel, Darren J. Perkins, and Stefanie N. Vogel. "AMP-activated kinase (AMPK) promotes innate immunity and antiviral defense through modulation of stimulator of interferon genes (STING) signaling." *Journal of Biological Chemistry*292.1 (2017): 292-304.

Ranzato, Elia, Simona Martinotti, and Bruno Burlando. "Wound healing properties of jojoba liquid wax: an in vitro study." *Journal of ethnopharmacology* 134.2 (2011): 443-449. http://www.sciencedirect.com/science/article/pii/S0378874110009189?via%3Dihub.

Roberts, Lynne M., and Daniel C. Smith. "Ricin: the endoplasmic reticulum connection." *Toxicon* 44.5 (2004): 469-472 http://www.sciencedirect.com/science/arricle/pii/S0041010104002855?via%3Dihub.

Roux, Philippe P., and John Blenis. "ERK and p38 MAPK-activated protein kinases: a family of protein kinases with diverse biological functions." *Microbiology and molecular biology reviews* 68.2 (2004): 320-344.

Simmons, Barbara M., P. D. Stahl, and John H. Russell. "Mannose receptor-mediated uptake of ricin toxin and ricin A chain by macrophages. Multiple intracellular pathways for a chain translocation." *Journal of Biological Chemistry* 261.17 (1986): 7912-7920.

Singh, Davinder P., et al. "Activation of multiple antiviral defence mechanisms by salicylic acid." *Molecular plant pathology* 5.1 (2004): 57-63. http://onlinelibrary.wiley.com/doi/10.1111/j.1364-3703.2004.00203.x/abstract.

Taylor, Kathryne E., and Karen L. Mossman. "Cellular protein WDR11 interacts with specific herpes simplex virus proteins at the trans-Golgi network to promote virus replication." *Journal of virology* 89.19 (2015): 9841-9852.

Teuton, Jeremy R., and Curtis R. Brandt. "Sialic acid on herpes simplex virus type 1 envelope glycoproteins is required for efficient infection of cells." *Journal of virology* 81.8 (2007): 3731-3739.

Uchida, Tsuyoshi, Eisuke Mekada, and Yoshio Okada. "Hybrid toxin of the A chain of ricin toxin and a subunit of Wistaria floribunda lectin. Possible importance of the hydrophobic region for entry of toxin into the cell." *Journal of Biological Chemistry* 255.14 (1980): 6687-6693.

Umaiyal, M. Pooja, et al. "Anti Microbial Activity of Jojoba Oil against Selected Microbes: An Invitro Study." *J. Pharm. Sci. & Res* 8.6 (2016): 528-529.

Wikipedia contributors. "PI3K/AKT/mTOR pathway." *Wikipedia, The Free Encyclopedia*. Wikipedia, The Free Encyclopedia, Oct. 14, 2017. Web. Jan. 4, 2018. From: https://en.wikipedia.org/wiki/PI3K/AKT/mTOR_pathway.

Wikipedia contributors. "Salicylic acid." *Wikipedia, The Free Encyclopedia*. Wikipedia, The Free Encyclopedia, Dec. 21, 2017. Web. Jan. 5, 2018. From: https://en.wikipedia.org/wiki/Salicylic_acid.

Wikipedia contributors. "Sialic acid." *Wikipedia, The Free Encyclopedia*. Wikipedia, The Free Encyclopedia, Sep. 11, 2017. Web. Jan. 4, 2018. From: https://en.wikipedia.org/wiki/Sialic_acid#Immunity.

Zhou, Ya-Qun, et al. "Cellular and molecular mechanisms of caicium/calmodulin-dependent protein kinase II in chronic pain." *Journal of Pharmacology and Experimental Therapeutics* 363.2 (2017): 176-183.

\* cited by examiner

PERSONAL-LUBRICATING MATERIAL AND METHOD FOR LUBRICANT MANUFACTURE

CROSS REFERENCE TO RELATED APPLICATIONS

Reference Cited [Referenced By]

U.S Patent Documents

U.S. Pat. No. 8,668,913 Ahmad, et al. Mar. 11, 2014
U.S. Pat. No. 8,636,982 Tamarkin, et al. Jan. 28, 2014
U.S. Pat. No. 8,540,970 Rodriguez-Vilaboa Sep. 24, 2013
U.S. Pat. No. 8,518,376 Tamarkin, et al. Aug. 27, 2013
U.S. Pat. No. 8,486,374 Tamarkin, et al. Jul. 16, 2013
U.S. Pat. No. 8,343,945 Tamarkin, et al. Jan. 1, 2013
U.S. Pat. No. 8,044,156 Tamareselvy, et al. Oct. 25, 2011
U.S. Pat. No. 8,029,812 Sunkara Oct. 4, 2011
U.S. Pat. No. 8,021,650 Tamareselvy, et al. Sep. 20, 2011
U.S. Pat. No. 7,423,082 Lai, et al. Sep. 9, 2008
U.S. Pat. No. 7,378,479 Tamareselvy, et al. May 27, 2008
U.S. Pat. No. 7,285,517 Ahmad, et al. Oct. 23, 2007
U.S. Pat. No. 5,512,289 Tseng, et al. Apr. 30, 1996

PARENT CASE TEXT

This application claims the benefit of provisional application Ser. No. 61/793,322 filed on Mar. 15, 2013

STATEMENT REGARDING FEDERALLY SPONSORED RESEARCH OR DEVELOPMENT

Not applicable.

REFERENCE TO SEQUENCE LISTING, TABLE OR COMPUTER LISTING

Not applicable.

BACKGROUND OF THE INVENTION

This invention addresses the personal or lubricant industry and more particularly the composition and manufacture of personal or patient lubricant colloquially known as "lube". Personal lubricant is useful for lubrication during intimate contact or when lubrication is required for the insertion of catheters, colostomy bags and similar medical devices or during ultrasound or similar procedure needing improved skin conduction and surface lubrication to prevent chafing.

Water soluble lubes are generally easy to clean and non-staining but react to friction by de-stabilizing and/or being absorbed by the skin and/or being dissolved by natural lubrication created by mucous membranes or other bodily fluids. This happens at a sufficient rate that re-application is often required during some activities such as coitus. Such an interruption is generally regarded as undesirable.

Further, catheter users who use lube to ease insertion of catheter devices can suffer significant discomfort during the removal of said devices since the lube that eased insertion has largely been absorbed or dissolved by the time of said removal.

Some lubricants currently used in the manufacture of lube (such as silicone) are not water soluble and therefore last much longer as a lubricant on skin as they are not readily dissolved by bodily fluids which are mostly water based. However, these product are not as desirable as water based lubes for both cleaning and biodegradability and their effect on certain polymers used in medical devices or common prophylactics.

Other ingredients commonly used in both types of lube include parabens which though anti-microbial are proving not to be benign when metabolized. In both cases it is possible that silicones and parabens may gradually penetrate skin potentially causing damage to cells. Further, silicone, propylene glycol and numerous other synthetic ingredients can cause an allergic reaction in a significant percentage of the population. It is also common practice to manufacture lube as a transparent product which though desirable in certain applications, make it difficult to see and therefore apply evenly to objects or skin.

Therefore it would be desirable to have a lube that eliminates the need for use of most synthetic ingredients and combines the most desirable characteristics of water soluble and oil based lubes in a formulation that inherently hinders the growth of microorganisms and is easy to apply evenly.

BRIEF SUMMARY OF THE INVENTION

The invention relates to a novel composition and method of manufacture whereby said composition may then be applied to one or more body parts of one or more individuals in order to ease the insertion of devices or body parts into a bodily cavity or orifice acting as a lubricant, typically during some form of intimate activity or during the process of intubation or catheterization. The invention is largely composed of natural ingredients blended in a unique ratio using a unique method that blends oils in a manner that allows them to combine several desirable features yet also be dissolvable with water. This invention is created as a stable, non-toxic, antimicrobial, organic suspension, which can be used as a substitute for current lubricants, yet provides health advantages through the use of organic and naturally derived ingredients that are friendlier to the human metabolism.

BRIEF DESCRIPTION OF THE SEVERAL VIEWS OF THE DRAWING

Not applicable.

DETAILED DESCRIPTION OF THE INVENTION

This invention bridges the gap between two separate types of lube commonly in use; those that are oil based and those that are water based. Traditionally, oil based lubes were derived from natural or synthetic (eg. Silicone) sources and where known to be long lasting. Water based lubes were easier to clean up and are often non-staining. The invention combines several ingredients that have desirable properties which when combined create a lube with numerous combined advantages over those currently available such as antifungal, antibacterial, antiviral, anti-oxidant and analgesic properties.

The invention eliminates the need to use known carcinogens in common lubes that use few certified organic ingredients. The invention uses organic ingredients but does not use microbe affable organic ingredients such as agar or butter. The invention does not use polymers that are acknowledged as damaging to common prophylactics such as latex Condoms.

The invention is non-transparent and thus designed to be easy to apply evenly. The invention is both water soluble and non-staining allowing for easy cleanup. The invention is also environmentally friendly as it is thoroughly biodegradable after disposal.

The invention offers performance enhancements over traditional personal—lubricants due to the differing absorption rates of it ingredients. With some ingredients absorbing faster, others float above those absorbed layers to provide a more lasting effect. Also the aforementioned varying rates offer multi-stage lubrication which creates a gentle increase in pleasurable friction which is desirable during sexual activity. The invention is long lasting and reduces or eliminates the need for reapplication common to existing water soluble personal lubricants.

One embodiment of this invention is formulated using an oil and a wax ester, a poly-saccharide, a natural sweetener that isn't a nutritive source for yeast or bacteria, water and a stabilizing agent, which are then mixed together in varying proportions using specialized rates and temperature controls to achieve optimal viscosity, desired density and solubility. The contents are then introduced to filling machine where they are mixed and then put into sealed containers.

Another embodiment of the formulation is a two part lubricant. The first being more readily absorbed by the skin, sinks into the surface layers forming a seal that prevents the other oil from being absorbed. The other oil, though not incompatible, is resistant to being dissolved by natural lubrication and forms a stable lubricious layer between the sealed layers of skin that rub against each other. This results in a lubricating layer that lasts significantly longer than traditional single stage personal lubricants.

Another embodiment of the formulation is offered as long lasting lube for the benefit of catheter users to allow for easier withdrawal unlike water based lubricants which though functional during insertion, provide no lubrication during withdrawal of the catheter; a process that can be quite painful.

Another embodiment of the formulation is to have the consistency of a lotion and be non-transparent to be easily seen so as to aid in the even application of the lube.

The present embodiments, described in the foregoing, satisfies the need within the art by providing a safe lube that is friendly to the body and discourages the growth of bacteria, yeast and fungus, is condom safe, performs better and is easier to thoroughly clean than that which is currently available.

The lube formulation of the invention offers a variety of benefits not currently satisfied in the marketplace, and provides a new method for greatly reducing the risk of STD posed by commonly used lubes which are not considered safe for use with condoms. Also, being intrinsically antimicrobial, it lessons the possibility of yeast infection and is very friendly to the mucosa of the vagina and urethra.

The lube formulation also reduces the potential for staining and therefore damaging clothing/bedding by having easy water cleanup. The lube formulation is also environmentally "friendly" as it is entirely organic and biodegradable.

The method of the invention describes a means for creating a lube that performs well as a lubricant, is long lasting yet varies the level of lubricity in order to enhance enjoyment of the activity.

The invention is illustrated by the following example:

Example: Sexual Lubricant or "Lube"

The ingredients are combined at a temperature of 40 to 80 degrees Celsius. The components are added together with an Ingredient % of castor oil at 26.00, Jojoba oil (commonly called an oil though actually a wax ester) at 20.00, Glycerin at 22.00, Water at 25.00, emulsifying organic resin Optiflo H370VF at 4.00, Pectin at 3.00. The final mixture, though based on two oils is water soluble and has a PH value between and 5.75 and 6.50.

What is claimed is:

1. A lubricant comprising oils, a polysaccharide, a sweetener, a stabilizing agent, and water in a stable suspension, wherein:
   the oils consist of castor oil and jojoba oil;
   the lubricant does not contain any oils other than the castor oil and the jojoba oil;
   the sweetener comprises glycerin;
   the stabilizing agent comprises a resin; and
   the lubricant does not degrade latex, polyisoprene, and polyurethane condoms.

2. The lubricant of claim 1, wherein the polysaccharide comprises pectin.

3. The lubricant of claim 1, wherein the lubricant has a pH between 5.75 and 6.50.

4. The lubricant of claim 1, wherein the lubricant is water-soluble.

5. The lubricant of claim 1, wherein the lubricant is antimicrobial and is devoid of parabens.

6. The lubricant of claim 1, wherein the lubricant is devoid of parabens, agar, butter, polymers that damage latex, silicone, and propylene glycol.

7. A lubricant comprising castor oil, jojoba oil, pectin, glycerin, and a resin in a stable suspension, wherein the lubricant does not contain any oils other than the castor oil and the jojoba oil, and wherein the lubricant does not degrade latex, polyisoprene, and polyurethane condoms.

8. The lubricant of claim 7, wherein the lubricant has a pH between 5.75 and 6.50.

9. The lubricant of claim 7, wherein the lubricant is water-soluble.

10. The lubricant of claim 7, wherein the lubricant is devoid of parabens, agar, butter, polymers that damage latex, silicone, and propylene glycol.

11. The lubricant of claim 7, wherein the lubricant is antimicrobial and is devoid of parabens.

12. A condom-safe, antimicrobial lubricant consisting essentially of castor oil, jojoba oil, pectin, glycerin, water, and a resin in a stable suspension, wherein the lubricant does not contain any oils other than the castor oil and the jojoba oil, wherein the lubricant does not degrade latex, polyisoprene, and polyurethane condoms, and wherein the lubricant is antimicrobial and is devoid of parabens.

13. The lubricant of claim 12, wherein the lubricant has a pH between 5.75 and 6.50.

14. The lubricant of claim 12, wherein the lubricant is water-soluble.

15. The lubricant of claim 12, wherein the lubricant is devoid of parabens, agar, butter, polymers that damage latex, silicone, and propylene glycol.

* * * * *